(12) United States Patent
Andersen et al.

(10) Patent No.: US 9,420,806 B2
(45) Date of Patent: Aug. 23, 2016

(54) BUFFERED GUM BASE FOR HIGH PH RELEASE

(75) Inventors: Carsten Andersen, Veijle (DK); Gitte Lorenzen, Vejle Øst (DK); Nicolai Arent, Horsens (DK); Bitten Thorengaard, Vejle Øst (DK); Helle Wittorff, Vejle Øst (DK)

(73) Assignee: Fertin Pharma A/S, Vejle (DK)

( * ) Notice: Subject to any disclaimer, the term of this patent is extended or adjusted under 35 U.S.C. 154(b) by 202 days.

(21) Appl. No.: 13/330,452

(22) Filed: Dec. 19, 2011

(65) Prior Publication Data

US 2012/0087875 A1    Apr. 12, 2012

Related U.S. Application Data

(63) Continuation of application No. PCT/DK2009/000146, filed on Jun. 19, 2009.

(51) Int. Cl.
```
A61K 9/68      (2006.01)
A61K 9/00      (2006.01)
A61K 9/22      (2006.01)
A61K 31/465    (2006.01)
A61P 25/34     (2006.01)
A23G 4/06      (2006.01)
A23G 4/08      (2006.01)
A23G 4/12      (2006.01)
A23G 4/20      (2006.01)
```

(52) U.S. Cl.
CPC ........... *A23G 4/064* (2013.01); *A23G 4/06* (2013.01); *A23G 4/08* (2013.01); *A23G 4/126* (2013.01); *A23G 4/20* (2013.01); *A61K 9/0058* (2013.01)

(58) Field of Classification Search
None
See application file for complete search history.

(56) References Cited

U.S. PATENT DOCUMENTS

| | | | |
|---|---|---|---|
| 2,489,147 A | 11/1949 | Lougovoy |
| 5,227,154 A | 7/1993 | Reynolds |
| 5,300,305 A | 4/1994 | Stapler et al. |
| 5,378,131 A | 1/1995 | Greenberg |
| 6,471,945 B2 | 10/2002 | Luo et al. |
| 6,479,071 B2 | 11/2002 | Holme et al. |
| 6,485,739 B2 | 11/2002 | Luo et al. |
| 6,685,916 B1 | 2/2004 | Holme et al. |
| 6,696,044 B2 | 2/2004 | Luo et al. |
| 6,733,818 B2 | 5/2004 | Luo et al. |
| 6,846,500 B1 | 1/2005 | Luo et al. |
| 2001/0043907 A1 | 11/2001 | Luo et al. |
| 2002/0071858 A1 | 6/2002 | Luo et al. |
| 2002/0098157 A1 | 7/2002 | Holme et al. |
| 2002/0159955 A1 | 10/2002 | Luo et al. |
| 2003/0099741 A1 | 5/2003 | Gubler |
| 2003/0124064 A1 | 7/2003 | Luo et al. |
| 2003/0157213 A1 | 8/2003 | Jenkins |
| 2003/0206993 A1 | 11/2003 | Gubler |
| 2003/0215417 A1 | 11/2003 | Uchiyama et al. |
| 2004/0081713 A1 | 4/2004 | Maxwell et al. |
| 2004/0136928 A1 | 7/2004 | Holme et al. |
| 2005/0008732 A1 | 1/2005 | Gebreselassie et al. |
| 2005/0025721 A1 | 2/2005 | Holme et al. |
| 2007/0269492 A1* | 11/2007 | Steen et al. ............... 424/440 |

FOREIGN PATENT DOCUMENTS

| | | | |
|---|---|---|---|
| WO | 0013662 A2 | 3/2000 |
| WO | 0025598 A1 | 5/2000 |
| WO | 02102357 A1 | 12/2002 |
| WO | WO 2006000232 A1 * | 1/2006 |
| WO | 2006058536 A1 | 6/2006 |
| WO | WO 2007076856 A1 * | 7/2007 |
| WO | 2009080022 A1 | 7/2009 |

OTHER PUBLICATIONS

International Search Report and Written Opinion of the International Searching Authority; Application No. PCT/DK2009/000146; Issued: Mar. 3, 2010; Mailing Date: Mar. 11, 2010; 9 pages.

* cited by examiner

*Primary Examiner* — Frederick Krass
*Assistant Examiner* — Michael P Cohen
(74) *Attorney, Agent, or Firm* — St. Onge Steward Johnston and Reens, LLC

(57) ABSTRACT

A chewing gum composition with high pH-release includes an insoluble gum base matrix and a soluble bulk portion, wherein the gum base matrix and the bulk portion is mixed and extruded to form a final chewing gum core, and wherein the gum base matrix is buffered before mixing with the bulk portion. Furthermore, a method of producing a chewing gum core, wherein a gum base matrix and a bulk portion is mixed and extruded to form a final chewing gum core, and wherein the gum base matrix is buffered before mixing with the bulk portion, and the gum base matrix includes a first amount of buffer from 2 to 20 percent by weight of the gum base matrix before mixing with the bulk portion.

13 Claims, No Drawings

BUFFERED GUM BASE FOR HIGH PH RELEASE

CROSS-REFERENCE TO RELATED APPLICATIONS

The present application is a continuation of pending International patent application PCT/DK2009/000146 filed on Jun. 19, 2009 which designates the United States and the content of which is incorporated herein by reference.

FIELD OF THE INVENTION

The present invention relates to the field of chewing gum. In particular, the present invention pertains to a formulation and method which may be used to extend a high pH level in the oral saliva for longer periods.

BACKGROUND OF THE INVENTION

A traditional way of including a buffer in a chewing gum formulation is by adding the buffer in the chewing gum formulation only after the gum base has been prepared. This may be done by adding a buffer while mixing an insoluble gum base matrix with a soluble bulk portion of the chewing gum formulation, or by adding buffer to a bulk portion and then mixing the bulk portion with a gum base matrix. In the alternative, this may also be done by adding buffer in a compressed formulation or by adding buffer to an outer coating of a chewing gum.

WO 02/102357 describes a coated chewing gum formulation suitable for rapid release of nicotine to a human subject by the addition of a buffer in the chewing gum formulation. One of the ways suggested in order to include the buffer in the chewing gum formulation is by adding the buffer to the coating of a final chewing gum core. Also, it is exemplified that in addition to including buffer to the coating of the final chewing gum core, a buffer may additionally be added together with a pre-prepared gum base (Cafosa Gum S/A) and other ingredients in the chewing gum formulation. However, the document does not disclose or suggest means for obtaining a high pH level for longer periods and means for obtaining a higher loading capacity of buffer without compromising the stability of the final chewing gum. Furthermore, the document is silent about how to obtain a buffered chewing gum without compromising the quality of the chewing gum, such as the texture, sensorial acceptance or taste of alkaline buffer in the chewing gum.

SUMMARY OF THE INVENTION

Accordingly, there is provided a chewing gum composition with high pH-release, the chewing gum composition comprising an water insoluble gum base matrix and a water soluble bulk portion, wherein the gum base matrix and the bulk portion is mixed and extruded to form a final chewing gum core, and wherein the gum base matrix is buffered before mixing with the bulk portion.

Furthermore, there is provided a chewing gum composition with high pH-release, the chewing gum composition comprising an water insoluble gum base matrix and a water soluble bulk portion, wherein the gum base matrix and the bulk portion is mixed and extruded to form a final chewing gum core, and wherein the gum base matrix is buffered before mixing with the bulk portion, the gum base matrix comprises a first amount of buffer from 2 to 20 percent by weight of the gum base matrix before mixing with the bulk portion, and wherein the chewing gum composition comprises a second amount of buffer from 1 to 5 percent by weight of the chewing gum composition, and wherein the chewing gum composition comprises nicotine polacrilex resin and sodium carbonate.

Additionally, there is provided a method of producing a chewing gum core according to the claims hereof, wherein a gum base matrix and a bulk portion is mixed and extruded to form a final chewing gum core, and wherein the gum base matrix is buffered before mixing with the bulk portion, and the gum base matrix comprises a first amount of buffer from 2 to 20 percent by weight of the gum base matrix before mixing with the bulk portion.

Finally, the invention relates to gum base pellet comprising a water insoluble gum base matrix wherein the gum base pellet comprises a first amount of buffer.

DETAILED DESCRIPTION OF THE INVENTION

Surprisingly, it has been seen that buffering the gum base matrix before the gum base matrix is mixed with the bulk portion provides several important advantages compared to formulations in which buffering takes place only after the gum base matrix has been prepared as disclosed in the prior art.

One of the advantages of the present invention is that a higher pH level may be obtained for longer periods compared to the prior art. This may be important in the pharmaceutical field if an active pharmaceutical ingredient depends on the pH level to give the required release. It may also be appreciated in order to obtain a pH level in the oral cavity of a human subject which may have a local function, for instance to prevent caries, plaque formation on the teeth, or other local disorders in the oral cavity. A high pH level may also prevent acidic conditions in the stomach, or be used in combination with other ingredients to help disorders in a human subject.

According to the present invention, the chewing gum formulation is prepared by extrusion and the extruded formulation is formed to give a final chewing gum core. In the present context the final chewing gum core is prepared after extrusion by for instance rolling and scoring the extruded chewing gum formulation in a continuous step to give the final chewing gum core. Compressed chewing gum techniques are not within the scope of the invention.

It is essential according to the present invention that an amount of buffer is added in the process of preparing the gum base matrix and not only after the gum base matrix has been prepared. Highly surprisingly, the loading capacity of buffer by using this approach is very high. According to the present invention the addition of buffer in the gum base may give a high, extended release of pH. Side effects as sensorial sense of a alkaline substance may be avoided according to the present invention, and the stability of the chewing gum formulation may be improved compared to the prior art.

Furthermore, it was highly surprising to the inventors of the present invention that it was actually possible to add buffer according to the invention in the preparation of the gum base, without the gum base system being disrupted. Accordingly, it was not foreseen that it was likely that the gum base matrix would be stable when adding buffer according to the invention.

The reason for the high loading capacity of the gum base matrix is not known, but the inventors of the present invention has seen that a very high amount of buffer may be incorporated in the chewing gum core instead of adding the buffer in the mixture step of gum base matrix and the soluble bulk portion, or by adding the buffer to an outer coating as disclosed in the prior art.

One of the greatest advantages of the present invention is that is solves the drawbacks of the prior art in one and the same solution. The great benefit of the present invention is that a high pH release is obtained and at the same time an extended pH release is obtained. The solution is a long felt need in the prior art, since the prior art typically pertains to either obtaining a high release for shorter periods or obtaining an extended release with lower release level. The contradictory problem of obtaining a high pH release and obtaining an extended pH release at the same time is solved by the present invention.

In addition to the novel insight, the present invention at the same time provides an acceptable texture of the final chewing gum core, which until now has been impossible to obtain by adding a relative high amount of buffer in a chewing gum system. The great advantage is that the buffered chewing gum core according to the present invention does not compromise the quality of the chewing gum. The chewing gum according to the invention also provides for an improved sensorial acceptance which is not obtained in the prior art.

Without being bound by theory it is believed that the addition of the buffer to the gum base matrix according to the present invention delimits the drawbacks of the prior art, such as masking the taste of a alkaline buffer, which in turn gives the consumer an experience of an improved chewing gum formulation, and at the same time provides for a system with a higher loading capacity.

As used herein, the term "chewing gum formulation" intends to mean all chewable gum products.

The term "high pH-release" is intended to mean a pH level over time which is higher than obtained without adding buffer to the chewing gum system.

The term "buffered" intends to mean that the chewing gum system comprises an amount of buffer/buffering agent and thereby functions as a buffer system. A buffering agent in the present context is characterized by maintaining the pH level within certain relative constant pH values. In case of an alkaline buffer the pH level will be maintained at an alkaline level dependent on the pKa values in the buffer system. In case of an acidic buffer the pH level will be maintained at an acidic level dependent on the pKa values in the buffer system.

The term "in vivo chewing" intends to mean that the chewing gum system is chewed by a human subject in a experimental setup of trained test persons according to stastically principles and that either the saliva of the human subject is subject to measurements or the chewed chewing gum is subject to measurements of the amount of buffer or the pH level, the experimental setup being performed at a chewing frequency of 60 per minute.

The term "sustained" or "extended" is herein intended to mean prolonged over time.

The term "controlled release" is intended to mean a release of a substance from a gum by the aid of active chewing of the gum in the oral cavity of the subject, whereby the active chewing is controlling the amount of substance released.

The term "stability" is intended to mean under conditions of 40 degrees celcius and 70 percentage relative humidity during a period of 14 days.

The term "weight of the chewing gum formulation" or similar wording meaning the same is defined in the present context as weight of the chewing gum formulation, without including the weight of an outer coating, such as a hard coating, soft coating, and the like.

In some embodiments of the invention a loading capacity of 2 to 20 percent by weight of the gum base matrix may be achieved without affecting the stability of the chewing gum formulation. In some embodiments of the invention, such as when using sodium carbonate as the buffer, the stability of the chewing gum formulation may be affected if more that 20 percent by weight of the gum base matrix is applied. Without being bound by theory it is believed that a higher amount of buffer may affect the gum base matrix.

In some embodiments of the invention the first amount of buffer is from 2 to 20 percent by weight of the gum base matrix before mixing with the bulk portion, such as 2 to 10 percent, such as 3 to 8 percent, such as 4 to 8 percent, such as 5 to 8 percent, such as 2 to 15 percent, such as 4 to 15 percent, such as 4 to 12 percent.

To the surprise of the inventors of the present invention, it was seen that the stability of the final chewing gum formulation was not affected when using this high amount of buffer in the gum base matrix compared to adding the buffer for instance in the step of mixing the gum base matrix with the soluble bulk portion. In this case the loading capacity is apparently lower. Apparently, the stability of the chewing gum formulation is affected by using a lower dose of buffer if it is not included during the manufacture of the gum base matrix.

In some embodiments of the invention the second amount of buffer is from 1 to 5 percent by weight of the chewing gum formulation, such as 1 to 4 percent, such as 2 to 5 percent, such as 3 to 5 percent, such as 3 to 4 percent, such as 1 to 3 percent.

In some embodiments of the invention the second amount of buffer is contained in the chewing gum core and/or in an outer coating. The addition of a second buffer is important in some embodiments because the second buffer provides a synergistic function upon the first amount of buffer contained in the gum base matrix. The second amount of buffer also provides for an initial release of buffer which in some embodiments is important to obtain an initial peak of a high pH. This initial peak of a high pH gives a possibility to add active ingredients which in turn will release according to the peak of a high pH. This initial peak of a high pH also gives a possibility to obtain a quick high pH in the oral cavity which may be suitable in various applications. The initial peak of a high pH furthermore gives the possibility to supplement the first amount of buffer.

In some embodiments of the invention the pH level in the saliva is increased by 0.3 to 4 pH units, such as 0.5 to 2 pH units, within the initial 5 minutes of in vivo chewing of the chewing gum composition measured at a chewing frequency of 60 per minute. In some embodiments of the invention the pH level in the saliva is increased by 0.5 to 2 pH units, within the initial 3 minutes, such as within the initial 2 minutes, such as within the initial 1 minute, such as within the initial 30 seconds, preferably within the initial 1 to 2 minutes.

It is contemplated that the pH in a human subject is different from subject to subject. Accordingly, some subjects may have a pH in the oral cavity which is lower than other subjects. Therefore, the increase in pH value will depend on the subject in question, which in turn makes the distinction of an absolute pH value not so meaningful than the relative pH value, such as an increase in pH units.

According to the invention the presently preferred way of adding buffer to the gum base matrix is in the very beginning of preparing the gum base matrix. Thus, in some embodiments of the invention the gum base matrix comprises a first amount of buffer from 2 to 20 percent by weight of the gum base matrix before mixing with the bulk portion, the buffer added in the first 2 minutes of gum base preparation, such as 4 minutes, such as 10 minutes. In these embodiments agglomeration is avoided or limited to a low degree. The buffer may preferably be added as a filler in the beginning of gum base preparation.

In some embodiments the pH level in the saliva is above 8.0 within the initial 10 minutes of in vivo chewing of the chewing gum composition measured at a chewing frequency of 60 per minute, such as above 8.1, such as above 8.2 such as above 8.3, such as above 8.5, such as above 9.0.

In general the pH value of the saliva in a human subject is just below 7. In some embodiments of the invention a pH value above 8.0 is important to obtain conditions in the oral cavity for better oral hygiene. A pH above 8.0 is believed to prevent caries and lessen the symptoms of gingivitis, or other disorders in the oral cavity. In some other embodiments a pH above 8.0 is believed to lessen symptoms of acidic conditions in the stomach of a human subject. In some further embodiments a pH above 8.0 supports the release of additional ingredients in the chewing gum formulation, such as active ingredient, such as active pharmaceutical ingredients, such as nicotine.

In some embodiments of the invention the pH level in the saliva is above 8.0 within the initial 10 to 15 minutes of in vivo chewing of the chewing gum composition measured at a chewing frequency of 60 per minute, such as above 8.1, such as above 8.2 such as above 8.3, such as above 8.5, such as above 9.0.

In some further embodiments of the invention the pH level in the saliva is above 8.0 within the initial 10 to 20 minutes of in vivo chewing of the chewing gum composition measured at a chewing frequency of 60 per minute, such as above 8.1, such as above 8.2 such as above 8.3, such as above 8.5, such as above 9.0.

In some further embodiments of the invention the pH level in the saliva is above 8.0 within the initial 20 to 30 minutes of in vivo chewing of the chewing gum composition measured at a chewing frequency of 60 per minute, such as above 8.1, such as above 8.2 such as above 8.3, such as above 8.5, such as above 9.0.

In some embodiments of the invention the buffer is selected from the group consisting of a carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, tris buffer, amino acids, and mixtures thereof.

The buffer may to some extent be microencapsulated or otherwise coated as granules with polymers and/or lipids being less soluble in saliva than is the one or more buffering agents. Such microencapsulation controls the dissolution rate whereby is extended the time frame of the buffering effect. In order to increase the buffering capacity still further without correspondingly increasing the pH, one may in specific embodiments use a second or auxiliary buffering agent to the first buffering agent, such as e g sodium or potassium bicarbonate buffers.

However, in a presently preferred embodiment an alkaline buffer is preferred, such as sodium carbonate.

The first and the second buffer according to the invention may be the same, or the first buffer may be different from the second buffer. In the present context the first buffer may be more than one type of buffer, and the second buffer may be more than one type of buffer. Accordingly, the first buffer may be sodium carbonate and sodium bicarbonate, or other buffers, and the second buffer may be sodium carbonate and sodium bicarbonate, or other buffers.

In a presently preferred embodiment, the first buffer is sodium carbonate and the second buffer is sodium carbonate and sodium bicarbonate.

In a presently preferred embodiment the amount of the first buffer is 3 to 7.5 percent by weight of the gum base matrix and the buffer is sodium carbonate, and the amount of the second buffer is 1 to 3 percent by weight of the chewing gum composition and the buffer is sodium carbonate, and the amount of the second buffer is 0.5 to 1.5 percent by weight of the chewing gum composition and the buffer is sodium bicarbonate.

It is contemplated that the use of a first buffer in the gum base matrix and a second buffer in the chewing gum formulation, not added during the manufacture of the gum base matrix, gives a synergy in the sense that the pH profile is optimised. By adding buffer in a chewing gum formulation without adding buffer to the gum base matrix gives rise to an initial high pH peak which is a drawback for the consumer of the product since it gives a taste of the for instance a alkaline substance. This is avoided by adding both the first and the second buffer according to the invention.

According to the invention the presence of buffer allows in synergy with an active ingredient, such as an active pharmaceutical ingredient, to support the release. In particular when the active ingredient is dependent on pH, the buffer may support the release of the active ingredient so as to control the release of the active ingredient, such as an active pharmaceutical ingredient, such as nicotine.

Thus, according to some embodiments of the invention the chewing gum formulation comprises at least one active ingredient, such as an active pharmaceutical ingredient, such as nicotine or a nutraceutical.

In some embodiments of the invention, the saliva has a pH level above the $pK_a$ of said active ingredient within the initial 5 minutes of in vivo chewing of the chewing gum composition measured at a chewing frequency of 60 per minute. In case of the active ingredient being nicotine, the pH above the $pK_a$ allows an optimised release of nicotine.

In some other embodiments of the invention, the saliva has a pH level above the $pK_a$ of said active ingredient within the initial 10 minutes of in vivo chewing of the chewing gum composition measured at a chewing frequency of 60 per minute. In case of the active ingredient being nicotine, the pH above the $pK_a$ allows an optimised release of nicotine.

In some other embodiments of the invention, the saliva has a pH level above the $pK_a$ of said active ingredient within the initial 10 to 20 minutes of in vivo chewing of the chewing gum composition measured at a chewing frequency of 60 per minute. In case of the active ingredient being nicotine, the pH above the $pK_a$ allows an optimised release of nicotine.

In some other embodiments of the invention, the saliva has a pH level above the $pK_a$ of said active ingredient within the initial 20 to 30 minutes of in vivo chewing of the chewing gum composition measured at a chewing frequency of 60 per minute. In case of the active ingredient being nicotine, the pH above the $pK_a$ allows an optimised release of nicotine.

In one embodiment of the invention the active ingredient is nicotine in any form.

The nicotine in any form according to the invention may be selected from the group consisting of a nicotine salt, the free base form of nicotine, a nicotine derivative, such as a nicotine cation exchanger, such as nicotine polacrilex resin, a nicotine inclusion complex or nicotine in any non-covalent binding; nicotine bound to zeolites; nicotine bound to cellulose, such as microcrystalline, such as of microbial origin, or starch microspheres, and mixtures thereof.

The present invention in some embodiments pertains to the application of nicotine as an active pharmaceutical ingredient. In particular it has been seen that by using sodium carbonate as the first buffer according to the invention, the pH level raises to a relative higher level above the pKa value of nicotine compared to the prior art. Also, the pH level is extended for a long period of time when the buffer is incorporated in the gum base matrix. This allows a beneficial high release of nicotine over an extended period. Typically, if buffer is not included in the gum base matrix, the release of buffer is not so high and/or is not extended for a long period of time.

The high release of nicotine by incorporating the buffer in the gum base matrix was highly surprising to the inventors of the present invention. Due to the high and extended pH release the present invention may in some embodiments be seen as a new way of controlling the release of an active ingredient, such as nicotine.

The present invention serves to solve two problems which has not been solved in the prior art at the same time. In the prior art solutions have been provided to obtain a rapid release of active ingredients. However, these solutions have the drawback that the release rate is not extended for longer periods at the same time. In the prior art solutions have been provided to obtain an extended release of active ingredients. However, these solutions have the drawback that the release rate is not high enough at the same time. The present invention solves the drawbacks of the prior art in one and the same solution.

In some other embodiments of the invention the active ingredient is selected from the group consisting of phytochemicals, such as resveratrol and anthocyanine; herbals, such as green tea or thyme; antioxidants, such as polyphenols; micronutrients; mouth moisteners, such as acids; throat soothing ingredients; appetite suppressors; breath fresheners, such as zinc compounds or copper compounds; diet supplements; cold suppressors; cough suppressors; vitamins, such as vitamin A, vitamin C or vitamin E; minerals, such as chromium; metal ions; alkaline materials, such as carbonates; salts; herbals, dental care agents, such as remineralisation agents, antibacterial agents, anti-caries agents, plaque acid buffering agents, tooth whiteners, stain removers or desensitizing agents; and combinations thereof.

Furthermore, the invention provides a chewing gum composition with high pH-release, the chewing gum composition comprising an insoluble gum base matrix and a soluble bulk portion, wherein the gum base matrix and the bulk portion is mixed and extruded to form a final chewing gum core, and wherein the gum base matrix is buffered before mixing with the bulk portion, the gum base matrix comprises a first amount of buffer from 2 to 20 percent by weight of the gum base matrix before mixing with the bulk portion, and wherein the chewing gum composition comprises a second amount of buffer from 1 to 5 percent by weight of the chewing gum composition, and wherein the chewing gum composition comprises nicotine polacrilex resin and sodium carbonate.

Finally, the present invention provides for a method of producing a chewing gum core, wherein a gum base matrix and a bulk portion is mixed and extruded to form a final chewing gum core, and wherein the gum base matrix is buffered before mixing with the bulk portion, and the gum base matrix comprises a first amount of buffer from 2 to 20 percent by weight of the gum base matrix before mixing with the bulk portion.

According to the invention the method of producing a chewing gum core may include the embodiments mentioned in the context of the chewing gum formulation pertaining to the product claims of the present invention.

In particular the method of producing a chewing gum core may include a step of adding buffer during the preparation of the gum base matrix, such as within the initial 1 minute of manufacture.

According to an embodiment of the present invention buffer may be added during the preparation of the gum base matrix at elevated temperatures.

According to an embodiment of the present invention the temperature when adding buffer during gum base matrix preparation exceeds about 60° C.

In some embodiments of the present invention, the temperature when adding buffer during gum base matrix preparation exceeds about 80° C.

In further embodiments the temperature when adding buffer during gum base matrix preparation exceeds about 100° C.

According to provisions of the present invention the temperature when adding buffer during gum base matrix preparation is about 120° C.

In an embodiment of the present invention, the addition of buffer during the preparation of the gum base matrix is facilitated by the above mentioned elevated temperatures.

The gum base matrix according to the present invention may comprise two or more ingredients selected from the group consisting of elastomers, elastomer plasticizers, resins, polyvinyl acetate, hydrogenated resins, polyterpene, fillers, fats and waxes, or any combination thereof.

It should be noted that various concentrations of gum base matrix in the final chewing gum core may be applied within the scope of the invention.

According to the invention a preferred amount of gum base matrix in the final chewing gum core is above 30 percent by weight of the chewing gum core, such as above 35 percent by weight of the chewing gum core, such as above 40 percent by weight of the chewing gum core, such as above 45 percent by weight of the chewing gum core, such as about 40 percent by weight of the chewing gum core, such as about 47 percent by weight of the chewing gum core.

The composition of gum base formulations can vary substantially depending on the particular product to be prepared and on the desired masticatory and other sensory characteristics of the final product. However, typical ranges (% by weight) of the above gum base components are: 5 to 80% by weight elastomeric compounds, 5 to 80% by weight elastomer plasticizers, 0 to 40% by weight of waxes, 5 to 35% by weight softener, 0 to 50% by weight filler, and 0 to 5% by weight of miscellaneous ingredients such as antioxidants, colourants, etc. The gum base may comprise about 5 to about 95 percent, by weight, of the chewing gum, more commonly the gum base comprises 10 to about 60 percent, by weight, of the gum.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkane chains of the waxes.

The elastomer compounds may be of natural origin but are preferably of synthetic origin, preferably synthetic polyesters.

The elastomers (rubbers) employed in the gum base may vary depending upon various factors such as the type of gum base desired, the texture of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

According to the invention, the preferred molecular weight of the elastomers is below 500.000 (MW) to give a homogeneous product which is easier to manufacture and which provides an optimized release profile of pH, and/or active ingredients.

Natural resins may be used according to the invention and may be natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

However, in a preferred embodiment of the invention polyterpene resins may be avoided in order to give a homogeneous product which is easier to manufacture and which provides an optimized release profile of pH, and/or active ingredients.

Mixing, rolling and scoring may be done by a conventional procedure. Double sigma blade mixers are used for mixing the gum base with the other components of the formulation. The gum base may be softened in the mixer. By heat (from the heating jacket) and mixing, the gum base becomes plastic. So, the softened base is mixed with the liquid components, e g flavours, liquid, sorbitol and glycerol, optionally an active ingredient, such as nicotine in base form, and the solid materials, optionally active ingredient, such as nicotine in any form other than in liquid form, buffer, bulk sweetener, color as a powder mixture. The warm mass is discharged from the mixer in form of loaves stacked on trays on a truck and stored in a conditioned area until the next step starts. This is to cool the gum.

After this, the rolling and scoring takes place. The gum is extruded into a thick i sheet, which is rolled by multiple sets of calendar rolls to the correct thickness. The scoring rolls, usually two sets, cut the gum into the correct size.

The sheets are then transferred to a conditioned area on trays, where the sheets are i cooled to make them brittle enough to be broken. The conditioned gum sheets are then passed through a breaker, which is a rotating drum that parts the sheets into separate pieces of gum along the scores.

In an embodiment of the invention, said chewing gum formulation comprises said gum base matrix and one or more chewing gum ingredients.

In an embodiment of the invention, said chewing gum ingredients are selected from the group consisting of bulk sweeteners, flavors, dry-binders, tabletting aids, anti-caking agents, emulsifiers, antioxidants, enhancers, absorption enhancers, buffers, high intensity sweeteners, colors, or any combination thereof.

In an embodiment of the invention, the chewing gum formulation comprise one or more chewing gum ingredients selected from the group consisting of bulk sweeteners, flavors, dry-binders, tabletting aids, anti-caking agents, emulsifiers, antioxidants, enhancers, absorption enhancers, buffers, or any combination thereof.

Further useful chewing gum base components include antioxidants, e.g. butylated hydroxytoluene (BHT), butyl hydroxyanisol (BHA), propylgallate and tocopherols, and preservatives.

A gum base formulation may, in accordance with the present invention, comprise one or more softening agents e.g. sucrose esters including those disclosed in WO 00/25598, which is incorporated herein by reference, tallow, hydrogenated tallow, hydrogenated and partially hydrogenated vegetable oils, cocoa butter, degreased cocoa powder, glycerol monostearate, glyceryl triacetate, lecithin, mono-, di- and triglycerides, acetylated monoglycerides, lanolin, sodium stearate, potassium stearate, glyceryl lecithin, propylene glycol monostearate, glycerine, fatty acids (e.g. stearic, palmitic, oleic and linoleic acids) and combinations thereof. As used herein the term "softener" designates an ingredient, which softens the gum base or chewing gum formulation and encompasses waxes, fats, oils, emulsifiers, surfactants and solubilisers.

To soften the gum base further and to provide it with water-binding properties, which confer to the gum base a pleasant smooth surface and reduce its adhesive properties, one or more emulsifiers is/are usually added to the composition, typically in an amount of 0 to 18% by weight, preferably 0 to 12% by weight of the gum base. Useful emulsifiers can include, but are not limited to, glyceryl monostearate, propylene glycol monostearate, mono- and diglycerides of edible fatty acids, lactic acid esters and acetic acid esters of mono- and diglycerides of edible fatty acids, acetylated mono and diglycerides, sugar esters of edible fatty acids, Na-, K-, Mg- and Ca-stearates, lecithin, hydroxylated lecithin and the like and mixtures thereof are examples of conventionally used emulsifiers which can be added to the chewing gum base. In case of the presence of a biologically or pharmaceutically active ingredient as defined below, the formulation may comprise certain specific emulsifiers and/or solubilisers in order to disperse and release the active ingredient.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

A chewing gum base formulation may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

In an embodiment of the invention, said chewing gum composition comprises biodegradable gum base.

In an embodiment of the invention, the chewing gum core is provided with an outer coating.

In an embodiment of the invention, said outer coating is selected from the group consisting of hard coating, soft coating and edible film-coating or any combination thereof.

According to the invention the active ingredient may be selected from the group consisting of antihistamines, anti-smoking agents, agents used for diabetes, decongestants, peptides, pain-relieving agents, nausea-relieving agents, statins, or any combination thereof.

In an embodiment of the invention, wherein the pharmaceutically active ingredients are selected from the group consisting of cetirizine, levo cetirizine, nicotine, nicotine polacrilex, nicotine in combination with alkaline agents, metformine, metformine HCL, phenylephrine, GLP-1, exenatide, deca-peptide, KSL-W (acetat), fluor, chlorhexidine, or any combination thereof.

In an embodiment of the invention, the pharmaceutically active ingredients are selected from the group consisting of loratadine, des-loratadine, nicotine bitartrate, nicotine in combination with caffeine, nicotine antagonists, combinations thereof or compounds comprising one or more of these, pseudoephedrine, flurbiprofen, paracetamol, acetylsalicylsyre, Ibuprofen, antacida, cimetidine, ranitidine, ondansetron, granisetron, metoclopramid, simvastatin, lovastatin, fluvastatin, acyclovir, benzydamin, rimonabant, varenicline, sildenafil, naltrexone, fluor in combination with fruit acids, derivatives, salts or isomers of chlorhexidine, or any combination thereof.

In an embodiment of the invention, the chewing gum formulation comprises a pharmaceutically active ingredient in the form of nicotine polacrilex and the buffer in the form of sodium carbonate.

In an embodiment of the invention, at least a part of the pharmaceutically active ingredients are adhered to dry-binder particles.

In an embodiment of the invention, at least a part of said active ingredients are incorporated in the chewing gum core.

In an embodiment of the invention, said active ingredient is selected from the group consisting of anti-histamines, decongestants, smoking cessation aids, diabetes II agents, or any combination thereof.

In an embodiment of the invention, said active ingredient is selected from the group consisting of metformin, cetirizine, levo cetirizine, phenylephrine, flurbiprofen, nicotine, nicotine bitartrate, nicotine polacrilex, nicotine in combination with alkaline agents, nicotine in combination with caffeine, sodium picosulfate, fluor, fluor in combination with fruit acids, chlorhexidine, or any derivatives thereof, salts thereof, isomers thereof, nicotine antagonists, combinations thereof or compounds comprising one or more of these.

In an embodiment of the invention, said active ingredient is selected from the group consisting of ephedrine, pseudo ephedrine, caffeine, loratadine, sildenafil, simvastatin, sumatriptan, acetaminophen, calcium carbonate, vitamin D, ibuprofen, aspirin, alginic acid in combination with aluminum hydroxide and sodium bicarbonate, ondansetron, Tibolon, Rimonabant, Varenicline, allergenes, sitagliptin or any derivatives thereof, salts thereof, isomers thereof, combinations thereof or compounds comprising one or more of these.

In some embodiments, a delivery system may be included. In some embodiments, the ingredients may be encapsulated or otherwise included separately in different delivery systems. Alternatively, in some embodiments the ingredients may be encapsulated or otherwise included in the same delivery system. As another possibility, one or more of the ingredients may be free (e.g. unencapsulated) while one or more other ingredients may be encapsulated. A chewing gum according to the invention may include a group of ingredients for which managed release of the group during consumption of the chewing gum formulation is desired. Groups of two or more ingredients for which managed release from a chewing gum during consumption of the chewing gum may be desired include, but are not limited to: color and flavor, multiple flavors, multiple colors, cooling agent and flavor, warming agent and flavor, cooling agent and warming agent, cooling agent and high-intensity sweetener, warming agent and high-intensity sweetener, multiple cooling agents (e.g., WS-3 and WS-23, WS-3 and menthyl succinate), menthol and one or more cooling agents, menthol and one or more warming agents, multiple warming agents, high-intensity sweetener(s) and tooth whitening active(s), high-intensity sweetener(s) and breath-freshening active(s), an ingredient with some bitterness and a bitterness suppressor for the ingredient, multiple high-intensity sweeteners (e.g., acesulfame-k and aspartame), multiple tooth whitening active ingredients (e.g., an abrasive ingredient and an antimicrobial ingredient, a peroxide and a nitrate, a warming agent and a polyol, a cooling agent and a polyol, multiple polyols, a warming agent and micronutrient, a cooling agent and a micronutrient, a warming agent and a mouth moistening agent, a cooling agent and a mouth moistening agent, a warming agent and a throat care agent, a cooling agent and a throat care agent, a warming agent and a food acid, a cooling agent and food acid, a warming agent and an emulsifier/surfactant, a cooling agent and an emulsifier/surfactant, a warming agent and a color, a cooling agent and a color, a warming agent and a flavor potentiator, a cooling agent and a flavor potentiator, a warming agent with sweetness potentiator, a cooling agent with a sweetness potentiator, a warming agent and an appetite suppressant, a cooling agent and an appetite suppressant, a high-intensity sweetener and a flavor, a cooling agent and a teeth-whitening agent, a warming agent and a teeth-whitening agent, a warming agent and breath-freshening agent, a cooling agent and a breath-freshening agent, a cooling agent and an effervescing system, a warming agent and an effervescing system, a warming agent and an antimicrobial agent, a cooling agent and an antimicrobial agent, multiple anticalcums ingredients, multiple remineralization ingredients, multiple surfactants, remineralization ingredients with demineralization ingredients, acidic ingredients with acid buffering ingredients, anticalculus ingredients with antibacterial ingredients, remineralization ingredients with anticalculus ingredients, anticalculus ingredients with remineralization ingredients with antibacterial ingredients, surfactant ingredients with anticalculus ingredients, surfactant ingredients with antibacterial ingredients, surfactant ingredients with remineralization ingredients, surfactants with anticalculus ingredients with antibacterial ingredients, multiple types of vitamins or minerals, multiple micronutrients, multiple acids, multiple antimicrobial ingredients, multiple breath-freshening ingredients, breath-freshening ingredients and antimicrobial ingredients, multiple appetite suppressors, acids and bases that react to effervesce, a bitter compound with a high-intensity sweetener, a cooling agent and an appetite suppressant, a warming agent and an appetite suppressant, a high-intensity sweetener and an appetite suppressant, a high-intensity sweetener with an acid, a probiotic ingredient and a prebiotic ingredient, a vitamin and a mineral, a metabolic enhancement ingredient with a macronutrient, a metabolic enhancement ingredient with a micronutrient, an enzyme with a substrate, a high-intensity sweetener with a sweetness potentiator, a cooling compound with a cooling potentiator, a flavor with a flavor potentiator, a warming compound with a warming potentiator, a flavor with salt, a high-intensity sweetener with salt, an acid with salt, a cooling compound with salt, a warming compound with salt, a flavor with a surfactant, an astringent compound with an ingredient to provide a sensation of hydration, etc. In some embodiments, the multiple ingredients may be part of the same delivery system or may be part of different delivery systems. Different delivery systems may use the same or different encapsulating materials.

In some embodiments, antitussive ingredients such as chlophedianol hydrochloride, codeine, codeine phosphate, codeine sulfate, dextromethorphan, dextromethorphan hydrobromide, diphenhydramine citrate, and diphenhydramine hydrochloride, and combinations thereof can be included.

In some embodiments, throat soothing agents such as honey, propolis, aloe vera, glycerine, menthol and combinations thereof can be included. In still other embodiments, cough suppressants can be included. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants). In some embodiments, ingredients from either or both groups can be included.

In still other embodiments, antitussives can include, but are not limited to, the group consisting of codeine, dextromethorphan, dextrorphan, diphenhydramine, hydrocodone, noscapine, oxycodone, pentoxyverine and combinations thereof. In some embodiments, antihistamines can include, but are not limited to, acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, non-sedating antihistamines can include, but are not limited to, astemizole, cetirizine, ebastine, fexofenadine, loratidine, terfenadine, and combinations thereof.

In some embodiments, expectorants can include, but are not limited to, ammonium chloride, guaifenesin, ipecac fluid extract, potassium iodide and combinations thereof. In some embodiments, mucolytics can include, but are not limited to, acetylcycsteine, ambroxol, bromhexine and combinations thereof. In some embodiments, analgesic, antipyretic and anti-inflammatory agents can include, but are not limited to, acetaminophen, aspirin, diclofenac, diflunisal, etodolac, fenoprofen, flurbiprofen, ibuprofen, ketoprofen, ketorolac, nabumetone, naproxen, piroxicam, caffeine and mixtures thereof. In some embodiments, local anesthetics can include, but are not limited to, lidocaine, benzocaine, phenol, dyclonine, benzonotate and mixtures thereof. In some embodiments nasal decongestants and ingredients that provide the perception of nasal clearing can be included. In some embodiments, nasal decongestants can include but are not limited to phenylpropanolamine, pseudoephedrine, ephedrine, phenylephrine, oxymetazoline, and combinations thereof. In some embodiments ingredients that provide a perception of nasal clearing can include but are not limited to menthol, camphor, borneol, ephedrine, eucalyptus oil, peppermint oil, methyl salicylate, bornyl acetate, lavender oil, wasabi extracts, horseradish extracts, and combinations thereof. In some embodiments, a perception of nasal clearing can be provided by odoriferous essential oils, extracts from woods, gums, flowers and other botanicals, resins, animal secretions, and synthetic aromatic materials.

Typically, encapsulation of a throat care agent will result in a delay in the release of the predominant amount of the active ingredient during consumption of a chewing gum that includes the encapsulated throat care agent (e.g. as part of a delivery system added as an ingredient to the chewing gum). In some embodiments, the release profile of the ingredient (e.g. the dental care active ingredient) can be managed for a gum by managing various characteristics of the ingredient, delivery system containing the ingredient, and/or the chewing gum containing the delivery system and/or how the delivery system is made. For example, characteristics might include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In an embodiment of the invention, said active ingredient is selected from the group consisting of phytochemicals, such as resveratrol and anthocyanine; herbals, such as green tea or thyme; antioxidants, such as polyphenols; micronutrients; mouth moisteners, such as acids; throat soothing ingredients; appetite suppressors; breath fresheners, such as zinc compounds or copper compounds; diet supplements; cold suppressors; cough suppressors; vitamins, such as vitamin A, vitamin C or vitamin E; minerals, such as chromium; metal ions; alkaline materials, such as carbonates; salts; herbals, dental care agents, such as remineralisation agents, antibacterial agents, anti-caries agents, plaque acid buffering agents, tooth whiteners, stain removers or desensitizing agents; and combinations thereof.

In addition to essential oils and chemicals derived from them, in some embodiments, breath fresheners can include but are not limited to zinc citrate, zinc acetate, zinc fluoride, zinc ammonium sulfate, zinc bromide, zinc iodide, zinc chloride, zinc nitrate, zinc fluorosilicate, zinc gluconate, zinc tartarate, zinc succinate, zinc formate, zinc chromate, zinc phenol sulfonate, zinc dithionate, zinc sulfate, silver nitrate, zinc salicylate, zinc glycerophosphate, copper nitrate, chlorophyll, copper chlorophyll, chlorophyllin, hydrogenated cottonseed oil, chlorine dioxide, beta cyclodextrin, zeolite, silica-based materials, carbon-based materials, enzymes such as laccase, and combinations thereof. In some embodiments, the release profiles of probiotics can be managed for a gum including, but not limited to lactic acid producing microorganisms such as *Bacillus coagulans, Bacillus subtilis, Bacillus laterosporus, Bacillus laevolacticus, Sporolactobacillus inulinus, Lactobacillus acidophilus, Lactobacillus curvatus, Lactobacillus plantarum, Lactobacillus jenseni, Lactobacillus casei, Lactobacillus fermentum, Lactococcus lactis, Pedioccocus acidilacti, Pedioccocus pentosaceus, Pedioccocus urinae, Leuconostoc mesenteroides, Bacillus coagulans,*

*Bacillus subtilis, Bacillus laterosporus, Bacillus laevolacticus, Sporolactobacillus inulinus* and mixtures thereof. Breath fresheners are also known by the following trade names: Retsyn™, Actizol™, and Nutrazin™. Examples of malodor-controlling compositions are also included in U.S. Pat. No. 5,300,305 to Stapler et al. and in U.S. Patent Application Publication Nos. 2003/0215417 and 2004/0081713 which are incorporated in their entirety herein by reference for all purposes.

Typically, encapsulation of the breath-freshening ingredient will result in a delay in the release of the predominant amount of the active ingredient during consumption of a chewing gum that includes the encapsulated breath-freshening ingredient (e.g., as part of a delivery system added as an ingredient to the chewing gum composition). In some embodiments, the release profile of the ingredient (e.g., the breath-freshening ingredient) can be managed for a gum by managing various characteristics of the ingredient, delivery system containing the ingredient, and/or the chewing gum containing the delivery system and/or how the delivery system is made. For example, characteristics might include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, minerals can include but are not limited to sodium, magnesium, chromium, iodine, iron, manganese, calcium, copper, fluoride, potassium, phosphorous, molybdenum, selenium, zinc, and combinations thereof.

In some embodiments micronutrients can include but are not limited to L-carnitine, choline, coenzyme Q10, alpha-lipoic acid, omega-3-fatty acids, pepsin, phytase, trypsin, lipases, proteases, cellulases, and combinations thereof.

Antioxidants can include materials that scavenge free radicals. In some embodiments, antioxidants can include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

In some embodiments, phytochemicals can include but are not limited to cartotenoids, chlorophyll, chlorophyllin, fiber, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

In some embodiments dental care ingredients may be included (also known as oral care ingredients) and ny be tooth whiteners, stain removers, oral cleaning, bleaching agents, desensitizing agents, dental remineralization agents, antibacterial agents, anticaries agents, plaque acid buffering agents, surfactants and anticalculus agents. Non-limiting examples of such ingredients can include, hydrolytic agents including proteolytic enzymes, abrasives such as hydrated silica, calcium carbonate, sodium bicarbonate and alumina, other active stain-removing components such as surface-active agents, including, but not limited to anionic surfactants such as sodium stearate, sodium palminate, sulfated butyl oleate, sodium oleate, salts of fumaric acid, glycerol, hydroxylated lecithin, sodium lauryl sulfate and chelators such as polyphosphates, which are typically employed as tartar control ingredients. In some embodiments, dental care ingredients can also include tetrasodium pyrophosphate and sodium tripolyphosphate, sodium bicarbonate, sodium acid pyrophosphate, sodium tripolyphosphate, xylitol, sodium hexametaphosphate. In some embodiments, peroxides such as carbamide peroxide, calcium peroxide, magnesium peroxide, sodium peroxide, hydrogen peroxide, and peroxydiphospate are included. In some embodiments, potassium nitrate and potassium citrate are included. Other examples can include casein glycomacropeptide, calcium casein peptone-calcium phosphate, casein phosphopeptides, casein phosphopeptide-amorphous calcium phosphate (CPP-ACP), and amorphous calcium phosphate. Still other examples can include papaine, krillase, pepsin, trypsin, lysozyme, dextranase, mutanase, glycoamylase, amylase, glucose oxidase, and combinations thereof. Further examples can include surfactants such as sodium stearate, sodium ricinoleate, and sodium lauryl sulfate surfactants for use in some embodiments to achieve increased prophylactic action and to render the dental care ingredients more cosmetically acceptable. Surfactants can preferably be detersive materials which impart to the composition detersive and foaming properties. Suitable examples of surfactants are water-soluble salts of higher fatty acid monoglyceride monosulfates, such as the sodium salt of the monosulfated monoglyceride of hydgrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine. In addition to surfactants, dental care ingredients can include antibacterial agents such as, but not limited to, triclosan, chlorhexidine, zinc citrate, silver nitrate, copper, limonene, and cetyl pyridinium chloride. In some embodiments, additional anticaries agents can include fluoride ions or fluorine-providing components such as inorganic fluoride salts. In some embodiments, soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride can be included. In some embodiments, a fluorine-containing compound having a beneficial effect on the care and hygiene of the oral cavity, e.g., diminution of enamel solubility in acid and protection of the teeth against decay may also be included as an ingredient. Examples thereof include sodium fluoride, stannous fluoride, potassium fluoride, potassium stannous fluoride ($SnF_2$—KF), sodium hexafluorostannate, stannous chlorofluoride, sodium fluorozirconate, and sodium monofluorophosphate. In some embodiments, urea is included. Further examples are included in the following U.S. patents and U.S. published patent applications, the contents of all of which are incorporated in their entirety herein by reference for all purposes: U.S. Pat. No. 5,227,154 to Reynolds, U.S. Pat. No. 5,378,131 to Greenberg, U.S. Pat. No. 6,846,500 to Luo et al, U.S. Pat. No. 6,733,818 to Luo et al., U.S. Pat. No. 6,696,044 to Luo et al., U.S. Pat. No. 6,685,916 to Holme et al., U.S. Pat. No. 6,485,739 to Luo et al., U.S. Pat. No. 6,479,071 to Holme et al., U.S. Pat. No. 6,471,945 to Luo et al., U.S. Patent Publication Nos. 20050025721 to Holme et al., 2005008732 to Gebreselassie et al., and 20040136928 to Holme et al.

In an embodiment of the invention, said active ingredient is selected from the group consisting of di-peptides, tri-peptides, oligo-peptides, deca-peptides, deca-peptide KSL, deca-peptide KSL-W, amino acids, proteins, or any combination thereof.

In an embodiment of the invention, said active ingredient comprises a probiotic bacteria, such as *lactobacilli, bifidobacteria, lactococcus, streptococcus, leuconostoccus, pediococcus* or *enterococcus*.

In an embodiment of the invention, said active ingredient comprises a prebiotic, such as fructose, galactose, mannose, insulin or soy.

The following list discloses examples of active ingredients which can be classified according to the ATC classification mentioned above and which are active ingredients which may be used according to the invention: Ephedrine, Magaldrate, Pseudoephedrine, Sildenafil, Xylocaine, Benzalconium chloride, Caffeine, Phenylephrine, Amfepramone, Orlistat, Sibutramine, Acetaminophen, Aspirin, Aluminum amino acetate, Aluminum amino acetate in combination with Magnesium oxide, Aluminum oxide hydrate in combination with Magnesiumoxide, Calcium carbonate in combination with Magnesium hydroxide, Calciumcarbonate, Dihydroxy Aluminum sodium carbonate, Magnesiumoxide, Glitazones, Metformin, Chlorpromazine, Dimenhydrinat, Domperidone, Meclozine, Metoclopramide, Odansetron, Prednisolone, Promethazine, Acrivastine, Cetirizine, Cinnarizine, Clemastine, Cyclizine, Desloratadine, Dexchlorpheniramine, Dimenhydrinate, Ebastine, Fexofenadine, Ibuprofen, Levolevoproricin, Loratadine, Meclozine, Mizolastine, Promethazine, Miconazole, Vitamin B12, Folic acid, Ferro compounds, vitamin C, Chlorhexidine diacetate, Fluoride, Decapeptide KSL, Aluminum fluoride, Aminochelated calcium, Ammonium fluoride, Ammonium fluorosilicate, Ammonium monofluorphosphate, Calcium fluoride, Calcium gluconate, Calcium glycerophosphate, Calcium lactate, Calcium monofluorphosphate, Calciumcarbonate, Carbamide, Cetyl pyridinium chloride, Chlorhexidine, Chlorhexidine digluconate, Chlorhexidine Chloride, Chlorhexidine diacetate, CPP Caseine Phospho Peptide, Hexetedine, Octadecentyl Ammonium fluoride, Potassium fluorosilicate, Potassium Chloride, Potassium monofluorphosphate, Sodium bi carbonate, Sodium carbonate, Sodium fluoride, Sodium fluorosilicate, Sodium monofluorphosphate, Sodium tri polyphosphate, Stannous fluoride, Stearyl Trihydroxyethyl Propylenediamine Dihydrofluoride, Strontium chloride, Tetra potassium pyrophosphate, Tetra sodium pyrophosphate, Tripotassium orthophosphate, Trisodium orthophosphate, Alginic acid, Aluminum hydroxide, Sodium bicarbonate, Sildenafil, Tadalafil, Vardenafil, Yohimbine, Cimetidine, Nizatidine, Ranitidine, Acetylsalicylic acid, Clopidogrel, Acetylcysteine, Bromhexine, Codeine, Dextromethorphan, Diphenhydramine, Noscapine, Phenylpropanolamine, vitamin D, Simvastatin, Bisacodyl, Lactitol, Lactulose, Magnesium oxide, Sodium picosulfate, Senna glycosides, Benzocaine, Lidocaine, Tetracaine, Almotriptan, Eletriptan, Naratriptan, Rizatriptan, Sumatriptan, Zolmitriptan, Calcium, Chromium, Copper, Iodine, Iron, Magnesium, Manganese, Molybdenium, Phosphor, Selenium, Zinc, Nicotine, Nicotine bitartrate, Nicotine pftalate, Nicotine polacrilex, Nicotine sulphate, Nicotine tartrate, Nicotine citrate, Nicotine lactate, Chloramine, Hydrogenperoxide, Metronidazole, Triamcinolonacetonide, Benzethonium Chl., Cetyl pyrid. Chl., Chlorhexidine, Fluoride, Lidocaine, Amphotericin, Miconazole, Nystatin, Fish oil, Ginkgo Biloba, Ginseng, Ginger, Purple coneflower, Saw Palmetto, Cetirizine, Levocetirizine, Loratadine, Diclofenac, Flurbiprofen, Acrivastine Pseudoephedrine, Loratadine Pseudoephedrine, Glucosamine, hyaluronic acid, Decapeptide KSL-W, Decapeptide KSL, Resveratrol, Misoprostol, Bupropion, Nicotine, Ondansetron HCl, Esomeprazole, Lansoprazole, Omeprazole, Pantoprazole, Rabeprazole, Bacteria and the like, Loperamide, Simethicone, Acetylsalicylic acid and others, Sucralfate, Vitamin A, Vitamin B1, Vitamin B12, Vitamin B2, Vitamin B6, Biotin, Vitamin C, Vitamin D, Vitamin E, Folinic acid, Vitamin K, Niacin, Q10, Clotrimazole, Fluconazole, Itraconazole, Ketoconazole, Terbinafine, Allopurinol, Probenecid, Atorvastatin, Fluvastatin, Lovastatin, Nicotinic acid, Pravastatin, Rosuvastatin, Simvastatin, Pilocarpine, Naproxen, Alendronate, Etidronate, Raloxifene, Risedronate, Benzodiazepines, Disulfuram, Naltrexone, Buprenorphine, Codeine, Dextropropoxyphene, Fentanyl, Hydromorphone, Ketobemidone, Ketoprofen, Methadone, Morphine, Naproxen, Nicomorphine, Oxycodone, Pethidine, Tramadol, Amoxicillin, Ampicillin, Azithromycin, Ciprofloxacin, Clarithromycin, Doxycyclin, Erythromycin, Fusidic acid, Lymecycline, Metronidazole, Moxifloxacin, Ofloxacin, Oxytetracycline, Phenoxymethylpenicillin, Rifamycins, Roxithromycin, Sulfamethizole, Tetracycline, Trimethoprim, Vancomycin, Acarbose, Glibenclamide, Gliclazide, Glimepiride, Glipizide, Insulin, Repaglinide, Tolbutamide, Oseltamivir, Aciclovir, Famciclovir, Penciclovir, Valganciclovir, Amlopidine, Diltiazem, Felodipine, Nifedipine, Verapamil, Finasteride, Minoxidil, Cocaine, Buphrenorphin, Clonidine, Methadone, Naltrexone, Calciumantagonists, Clonidine, Ergotamine, n-blockers, Aceclofenac, Celecoxib, Dexiprofen, Etodolac, Indometacin, Ketoprofen, Ketorolac, Lornoxicam, Meloxicam, Nabumetone, Oiroxicam, Parecoxib, Phenylbutazone, Piroxicam, Tiaprofenic acid, Tolfenamic acid, Aripiprazole, Chlorpromazine, Chlorprothixene, Clozapine, Flupentixol, Fluphenazine, Haloperidol, Lithium carbonate, Lithium citrate, Melperone, Penfluridol, Periciazine, Perphenazine, Pimozide, Pipamperone, Prochlorperazine, Risperidone, Thioridizin, Fluconazole, Itraconazole, Ketoconazole, Voriconazole, Opium, Benzodiazepines, Hydroxine, Meprobamate, Phenothiazine, Aluminiumaminoacetate, Esomeprazole, Famotidine, Magnesium oxide, Nizatide, Omeprazole, Pantoprazole, Fluconazole, Itraconazole, Ketoconazole, Metronidazole, Amphetamine, Atenolol, Bisoprolol fumarate, Metoprolol, Metropolol, Pindolol, Propranolol, Auranofin, and Bendazac.

Further examples of useful active ingredients include active ingredients selected from the therapeutical groups comprising: Analgesic, Anaestetic, Antipyretic, Anti allergic, Anti-arrytmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestrant, Gastro-intestinal sedative, Sexual dysfunction agent, Desinfectants, Anti-diarrheal, Anti-anginal substance, Vasodilator, Anti-hypertensive agent, Vasoconstrictor, Migraine treating agent, Antibiotic, Tranquilizer, Ntipsychotic, Anti-tumor drug, Anticoagulant, Antithrombotic agent, Hypnotic, Sedative, Anti-emetic, Anti-, auseant, Anticonvulsant, Neuromuscular agent, Hyper and hypoglycaemic, Thyroid and antithyroid, Diuretic, Antispasmodic, Uterine relaxant, Anti-obesity agent, Anoretic, Spasnolytics, Anabolic agent, Erythropoietic agent, Antiasthmatic, Expectorant, Cough suppressant, Mucolytic, Anti-uricemic agent, Dental vehicle, Breath freshener, Antacid, Anti-diuretc, Anti-flatulent, Betablokker, Teeth Whitener, Enzyme, Co-enzyme, Protein, Energy booster, Fiber, Probiotics, Prebiotics, Antimicrobial agent, NSAID, Anti-tussives, Decongestrants, Anti-histamines, Expectorants, Anti-diarrheals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, and Sexual dysfunction agents.

Examples of useful active ingredients include: Casein glyco-macro-peptide (CGMP), Nicotine, Nicotine bitartrate, Nicotine sulphate, Nicotine tartrate, Nicotine pftalate, Nicotine lactate, Nicotinecitrate, Nicotine polacrilex, Triclosan, Cetyl pyridinium chloride, Domiphen bromide, Quarternary ammonium salts, Zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniramine-maleate, Carbinoxamine maleate, Clemastine fumarate, Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbrompheniamine, Guaifenesin, Ipecac, Potassium iodide, Terpin hydrate, Loperamide, Famotidine, Ranitidine, Omeprazole, Lansoprazole, Aliphatic alcohols, Barbiturates, Caffeine, Nicotine, Strychnine, Picrotoxin, Pentyenetetrazol, Phenyhydantoin, Phenobarbital, Primidone, Carbamazapine, Etoxsuximide, Methsuximide, Phensuximide, Trimethadione, Diazepam, Benzodiazepines, Phenacemide, Pheneturide, Acetazolamide, Sulthiame, Bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, Imipramine, Tranylcypromine, Phenelzine, Lithium, Sildenafil citrate, Tadalafil, and Vardenafil CL.

Examples of useful active ingredients include active ingredients selected from the groups of ace-inhibitors, antianginal drugs, anti-arrhythmias, anti-asthmatics, anti-cholesterolemics, analgesics, anesthetics, anticonvulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psycho-therapeutic agents, respiratory agents, sedatives, smoking cessation aids such as bromocriptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of active ingredients contemplated for use in the present invention can include antacids, H2-antagonists, and analgesics. For example, antacid dosages can be prepared using the ingredients calcium carbonate alone or in combination with magnesium hydroxide, and/or aluminum hydroxide. Moreover, antacids can be used in combination with H2-antagonists.

Analgesics include opiates and opiate derivatives, such as Oxycontin™, ibuprofen, aspirin, acetaminophen, and combinations thereof that may optionally include caffeine.

Other drug active ingredients for use in embodiments can include anti-diarrheals such as Immodium™ AD, anti-histamines, anti-tussives, decongestants, vitamins, and breath fresheners. Also contemplated for use herein are anxiolytics such as Xanax™, anti-psychotics such as Clozaril™ and Haldol™; non-steroidal anti-inflammatories (NSAID's) such as ibuprofen, naproxen sodium, Voltaren™ and Lodine™, anti-histamines such as Claritin™, Hismanal™, Relafen™, and Tavist™; antiemetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™, and CaH-antagonists such as Procardia™, Adalat™, and Calan™.

The popular H2-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients can include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts. A variety of nutritional supplements may also be used as active ingredients including virtually any vitamin or mineral. For example, vitamin A, vitamin C, vitamin D, vitamin E, vitamin K, vitamin B6, vitamin B12, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used. Examples of nutritional supplements that can be used as active ingredients are set forth in U.S. Patent Application Publication Nos. 2003/0157213 A1, 2003/0206993 and 2003/0099741 A1 which are incorporated in their entirety herein by reference for all purposes. Various herbals may also be used as active ingredients such as those with various medicinal or dietary supplement properties. Herbals are generally aromatic plants or plant parts and or extracts thereof that can be used medicinally or for flavoring. Suitable herbals can be used singly or in various mixtures. Commonly used herbs include Echinacea, Goldenseal, Calendula, Rosemary, Thyme, Kava Kava, Aloe, Blood Root, Grapefruit Seed Extract, Black Cohosh, Ginseng, Guarana, Cranberry, Ginko Biloba, St. John's Wort, Evening Primrose Oil, Yohimbe Bark, Green Tea, Ma Huang, Maca, Bilberry, Lutein, and combinations thereof.

In an embodiment of the invention, said chewing gum formulation comprises one or more encapsulation delivery systems.

In an embodiment of the invention, an amount of dry-binder is used to adhere API to bulk sweetener.

In one embodiment of the invention, the flavor may be used as taste masking in chewing gum comprising active ingredients, which by themselves have undesired taste or which alter the taste of the formulation.

Moreover the invention relates to gum base pellet comprising a water insoluble gum base matrix wherein the gum base pellet comprises a first amount of buffer.

Through the addition of buffer into the gum base pellets, a high pH-release chewing gum may be obtained when the chewing gum is based on the gum base pellets.

According to the invention the gum base pellet may include embodiments mentioned in the context of the chewing gum formulation pertaining to the product claims of the present invention where applicable.

According to the present invention the embodiments mentioned in the specification of this patent application may be combined according to the present invention.

The following non-limiting examples illustrate different variations of the present invention. The examples are meant for indicating the inventive concept; hence the mentioned examples should not be understood as exhaustive for the present invention.

EXAMPLE 1

Preparation of Gum Base

Gum base is prepared with varied content of buffer, and gum base is prepared without a content of buffer. A buffer has been added as outlined in table 1.

TABLE 1

Gum base matrix compositions.

|  | GB1 | GB2 | GB3 | GB4 | GB5 |
|---|---|---|---|---|---|
| Elastomer | 15.5 | 15.5 | 15.5 | 15.5 | 15.5 |
| PVA | 22 | 22 | 22 | 22 | 22 |
| Natural resin | 28 | 28 | 28 | 28 | 28 |
| Filler | 16.5 | 14 | 11.5 | 9 | 6.5 |
| $Na_2CO_3$-buffer | 0 | 2.5 | 5 | 7.5 | 10 |
| Emulsifier | 4 | 4 | 4 | 4 | 4 |
| Softener | 13.9 | 13.9 | 13.9 | 13.9 | 13.9 |
| Antioxidant | 0.1 (900 ppm) | 0.1 (900 ppm) | 0.1 (900 ppm) | 0.1 (900 ppm) | 0.1 (900 ppm) |

Amounts are given in percent by weight of each composition. GB = Gum Base

The preparation of the gum base is carried out by first adding a high-molecular weight elastomer, polyvinyl acetate, filler and sodium carbonate to a heated (about 120° C.) and running z-blade mixer. After about twenty minutes of mixing, natural resin is added to the running mixer and mixing is continued for about five minutes followed by addition of further natural resin. After about five minutes of continued mixing, emulsifier and further elastomer are added to the running mixer, and mixing is continued for about five minutes before addition of softener and antioxidant to the running mixer. Mixing is continued for about half an hour to one hour, and the final gum base mass is emptied from the mixer into coated or lined pans, extruded or cast into any desirable shape. Those skilled in the art will recognize that many variations of the above-described procedure may be followed.

EXAMPLE 2

Preparation of Chewing Gum

In the present example chewing gum is prepared with varied amounts of buffer, and chewing gum is prepared without a content of buffer. A buffer has been added as outlined in table 2. In the present example chewing gum is prepared with NPR (nicotine polacrilex resin), and chewing gum is prepared without NPR.

TABLE 2

Chewing gum compositions.

|  | CG 1 | CG 2 | CG 3 | CG 4 | CG 5 | CG 6 | CG 7 | CG 8 | CG 9 | CG 10 | CG 11 | CG 12 |
|---|---|---|---|---|---|---|---|---|---|---|---|---|
| GB1 | 40 |  |  |  |  |  |  |  |  | 40 | 40 | 40 |
| GB2 |  | 40 |  |  |  |  |  |  |  |  |  |  |
| GB3 |  |  | 40 | 40 |  |  |  |  |  |  |  |  |
| GB4 |  |  |  |  | 40 | 40 |  |  |  |  |  |  |
| GB5 |  |  |  |  |  |  | 40 | 40 |  |  |  |  |
| GB6 |  |  |  |  |  |  |  |  | 40 |  |  |  |
| Bulk Sweet | 54 | 52.6 | 53.6 | 52.6 | 53.6 | 52.6 | 55.6 | 52.6 | 52.6 | 49.6 | 48.6 | 46.6 |
| Buffer | 3 | 3 | 2 | 3 | 2 | 3 | 0 | 3 | 3 | 3 | 6 | 7 |
| Flavor | 3 | 3 | 3 | 3 | 3 | 3 | 3 | 3 | 3 | 3 | 3 | 3 |
| NPR | 0 | 1.4 | 1.4 | 1.4 | 1.4 | 1.4 | 1.4 | 1.4 | 1.4 | 1.4 | 1.4 | 1.4 |

Amounts are given in percent by weight of each composition. When buffer is added in the present example it is added together with the other chewing gum ingredients in the process of mixing the gum base from Example 1 with additional chewing gum ingredients. In the present example the buffer consists of two buffers, namely 1% sodium bicarbonate and varied amounts of sodiumcarbonate.
CG = Chewing gum

EXAMPLE 3

Sensory Evaluation

Chewing gum formulations were prepared according to example 2 containing various amounts of a first buffer in the gum base matrix and a various amounts of a second buffer in the chewing gum composition.

Chewing gum samples comprising the different gum base matrices and buffer amounts were tested by a panel of individual test persons.

TABLE 3

Sensory evaluations.

| | CG 1 | CG 2 | CG 3 | CG 4 | CG 5 | CG 6 | CG 7 | CG 8 | CG 9 | CG 10 | CG 11 | CG 12 |
|---|---|---|---|---|---|---|---|---|---|---|---|---|
| Buffer GB | 0 | 2.5 | 5 | 5 | 7.5 | 7.5 | 10 | 10 | 12.5 | 0 | 0 | 0 |
| Buffer CG | 3 | 3 | 2 | 3 | 2 | 3 | 0 | 3 | 3 | 3 | 6 | 7 |
| Sensory approval | +++ | +++ | +++ | +++ | +++ | ++ | ++ | + | +++ | − | − | − |

All values of buffer in the GB in percentage of the gum base matrix. All values of buffer in the CG in percentage of the chewing gum formulation.

All the chewing gum formulations were evaluated to be acceptable with regards to conventional chewing texture and overall taste sensation. The chewing gum formulations had the desired texture and taste profile when applying any of the buffer systems CG1 (placebo), CG2, CG3, CG4, CG5, CG6, CG7 and CG9. Samples comprising higher levels of buffer were evaluated to be hardly acceptable; CG10, CG11 and CG12, since the total high amount of buffer give a strong alkaline taste and corrosive feeling in the mouth.

EXAMPLE 4

In Vivo pH Profile

Table 4 shows that the pH profile is very dependent on the concentration of buffer (sodium carbonate and sodium bicarbonate) and where the buffer is added.

The target pH profile with high pH from beginning (buffer in the chewing gum composition) and extended pH in saliva is achieved by adding buffer in gum base matrix.

TABLE 4 pH In vivo measurements.

| Time | CG 1 | CG 2 | CG 3 | CG 4 | CG 5 | CG 6 | CG 7 | CG 8 | CG 9 | CG 10 | CG 11 | CG 12 |
|---|---|---|---|---|---|---|---|---|---|---|---|---|
| 0 min | 7.2 | 7.2 | 7.2 | 7.2 | 7.2 | 7.2 | 7.2 | 7.2 | 7.2 | 7.2 | 7.2 | 7.2 |
| 1 min | 7.6 | 8.1 | 8.2 | 8.6 | 8.3 | 9.4 | 7.5 | 9.2 | 7.4 | 8.1 | 8.3 | 8.5 |
| 5 min | 7.9 | 8.0 | 8.6 | 8.5 | 8.9 | 9.3 | 8.7 | 9.5 | 7.7 | 7.6 | 8.0 | 8.1 |
| 10 min | 7.7 | 8.0 | 8.5 | 8.6 | 8.9 | 9.3 | 8.7 | 9.5 | 7.5 | 7.6 | 7.7 | 7.9 |

All pH measurements are made in vivo, the in vivo profile is different from the in vitro pH profile due to the fact that sodium bicarbonate is continuously produced in saliva, hence neutralizing the contribution from sodium carbonate. The pH obtained in vivo upon chewing will be lower than in vitro.

What is claimed is:

1. Chewing gum composition for high pH-release, the chewing gum composition comprising a water insoluble gum base matrix and a water soluble bulk portion, wherein the gum base matrix and the bulk portion is mixed and extruded to form a final chewing gum core, and wherein the gum base matrix is buffered before mixing with the bulk portion, wherein the pH level in the saliva is above 8.0 after the initial 10 minutes of in vivo chewing of the chewing gum composition measured at a chewing frequency of 60 per minute, wherein the gum base matrix comprises a first amount of buffer from 2 to 20 percent by weight of the gum base matrix before mixing with the bulk portion and wherein the buffer loading capacity of the final chewing gum is greater than the buffer loading capacity of the same chewing gum formulation prepared by including the buffer during mixing with the bulk portion.

2. Chewing gum composition according to claim 1, wherein the chewing gum composition comprises an additional amount of buffer from 1 to 5 percent by weight of the chewing gum composition.

3. Chewing gum composition according to claim 2, wherein the additional amount of buffer is comprised in the chewing gum core, in an outer coating or both in the chewing gum core and in the outer coating.

4. Chewing gum composition according to claim 1, wherein the buffer is selected from the group consisting of a carbonate, glycerinate, phosphate, glycerophosphate, acetate, glyconate or citrate of an alkali metal, or ammonium, and mixtures thereof.

5. Chewing gum composition according to claim 1, wherein the buffer is sodium carbonate.

6. Chewing gum composition according to claim 1 further comprising at least one active ingredient.

7. Chewing gum composition according to claim 6, wherein the saliva has a pH above the $pK_a$ of said active ingredient within the initial 5 minutes of in vivo chewing of the chewing gum composition measured at a chewing frequency of 60 per minute.

8. Chewing gum composition according to claim 6, wherein the active ingredient is nicotine.

9. Chewing gum composition according to claim 8, wherein the nicotine is selected from the group consisting of a nicotine salt, the free base form of nicotine, a nicotine derivative, a nicotine inclusion complex or nicotine in any non-covalent binding; nicotine bound to zeolites; nicotine bound to cellulose, or starch microspheres, and mixtures thereof.

10. Chewing gum composition according to claim 6, wherein said active ingredient is selected from the group consisting of phytochemicals; herbals; antioxidants; mouth moisteners; throat soothing ingredients; appetite suppressors; breath fresheners; diet supplements; cold suppressors; cough suppressors; vitamins; minerals; metal ions; alkaline materials; salts; herbals, dental care agents; and combinations thereof.

11. Chewing gum composition according to claim 1, wherein the pH level in the saliva is increased by 0.5 to 2 pH units within the initial 5 minutes of in vivo chewing of the chewing gum composition measured at a chewing frequency of 60 per minute.

12. Chewing gum composition for high pH-release, the chewing gum composition comprising a water insoluble gum base matrix and a water soluble bulk portion, wherein the gum base matrix and the bulk portion is mixed and extruded to form a final chewing gum core, and wherein the gum base matrix is buffered before mixing with the bulk portion, the gum base matrix comprises a first amount of buffer from 2 to 20 percent by weight of the gum base matrix before mixing with the bulk portion, and wherein the chewing gum composition comprises an additional amount of buffer from 1 to 5 percent by weight of the chewing gum composition, and wherein the chewing gum composition comprises nicotine polacrilex resin and sodium carbonate, wherein the pH level in the saliva is above 8.0 after the initial 10 minutes of in vivo chewing of the chewing gum composition measured at a chewing frequency of 60 per minute, whereby a sustained release rate of nicotine is achieved after the initial 10 minutes of in vivo chewing and wherein the buffer loading capacity of the final chewing gum is greater than the buffer loading capacity of the same chewing gum formulation prepared by including the buffer during mixing with the bulk portion.

13. Method of producing a chewing gum core according to claim 1, wherein a gum base matrix and a bulk portion is mixed and extruded to form a final chewing gum core, and wherein the gum base matrix is buffered before mixing with the bulk portion, and the gum base matrix comprises a first amount of buffer from 2 to 20 percent by weight of the gum base matrix before mixing with the bulk portion.

* * * * *